(12) United States Patent
Joensen

(10) Patent No.: US 6,573,403 B1
(45) Date of Patent: Jun. 3, 2003

(54) PROCESS FOR PRODUCTION OF ACETIC ACID

(75) Inventor: Finn Joensen, Horsholm (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/647,398

(22) PCT Filed: Mar. 29, 1999

(86) PCT No.: PCT/EP99/02163

§ 371 (c)(1),
(2), (4) Date: Dec. 5, 2000

(87) PCT Pub. No.: WO99/50218

PCT Pub. Date: Oct. 7, 1999

Related U.S. Application Data

(60) Provisional application No. 60/080,211, filed on Mar. 31, 1998.

(51) Int. Cl.[7] .................................................. C07C 51/12
(52) U.S. Cl. ........................................ 562/519; 562/607
(58) Field of Search ................................ 562/519, 607

(56) References Cited

U.S. PATENT DOCUMENTS 4,514,336 A    4/1985  Ryan et al. ................. 260/413
5,488,143 A  * 1/1996  Uhm et al. .................. 560/232

FOREIGN PATENT DOCUMENTS

| EP | 0 031 606 A1 | 7/1981 |
| EP | 0 075 335 A1 | 3/1983 |
| EP | 0 075 337 A1 | 3/1983 |
| EP | 0 083 121 A1 | 7/1983 |
| EP | 0 085 204 A1 | 8/1983 |
| EP | 0 335 625 A2 | 10/1989 |
| EP | 0 372 993 A1 | 6/1990 |
| EP | 0 728 727 A1 | 8/1996 |
| FR | 2 058 060    | 5/1971 |

* cited by examiner

*Primary Examiner*—Samuel Barts
(74) *Attorney, Agent, or Firm*—Morgan, Lewis & Bockius LLP

(57) ABSTRACT

A process for producing acetic acid which comprises charging reactants methanol, dimethyl ether, methyl acetate or any mixture thereof into a reactor containing: (1) a rhodium carbonylation catalyst, (2) an alkyl iodide or alkyl bromide, and (3) a hydrogenation catalyst, and contacting the reactants with carbon monoxide and hydrogen to produce acetic acid.

3 Claims, No Drawings

PROCESS FOR PRODUCTION OF ACETIC ACID

This application is a 35 U.S.C. §371 filing of PCT Application No. PCT/EP99/02163, filed Mar. 29, 1999, which claims the benefit of U.S. Provisional Application No. 60/080,211, filed Mar. 31, 1998, both of which are herein incorporated by reference in their entirety.

The present invention relates to a method for the production of acetic acid with reduced formation of carbonyl impurities, especially acetaldehyde and acetone, by carbonylation of methanol and/or dimethyl ether and/or methyl acetate in the presence of a rhodium catalyst and a methyl halide.

Carbonylation processes in the presence of rhodium catalysts are known and described, for example in U.S. Pat. No. 3,768,329.

Carbonylation processes in the presence of ruthenium and osmium catalysts are known from GB Patent Nos. 1,234,641 and 2,029,409.

A carbonylation process combining rhodium as a carbonylation catalyst and ruthenium and/or osmium as a promoter for increasing reaction rate at specified conditions is, furthermore, known from EP 728,727.

The general object of this invention is to provide a process for carbonylation of methanol or reactive derivatives thereof with suppressed formation of undesired by-products, causing major separation problems, such as acetaldehyde and acetone, whereas certain by-products, which are easily separated and even may represent a valuable coproduct, such as propanoic acid are produced at rates higher than at the above undesired by-products.

Acetic acid is currently produced by catalytic carbonylation of methanol. The traditional catalyst system comprises a rhodium compound and a methyl halide promoter such as methyl iodide. Typically, the reaction is conducted at temperatures between 150° C. and 200° C. and pressures from 20–50 bar with the rhodium catalyst dissolved in the liquid reaction medium consisting mainly of acetic acid, water and methyl iodide. Under reaction conditions a number of interconversions between reactants and products proceeds, such as esterification and hydrolysis:

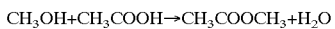

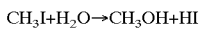

These reactions are, under reaction conditions, essentially governed by thermodynamic equilibrium. In accordance with the equations above the feedstock may consist of methanol, dimethyl ether+water, methyl acetate+water, or any mixture of methanol, dimethyl ether, methyl acetate and water.

The overall reaction takes place according to the equation:

Similar catalyst systems may be utilised in the synthesis of other carboxylic acids, e.g. propanoic acid by replacing methyl iodide promoter with ethyl iodide and replacing methanol with ethanol:

Thus, by replacing the alcohol feed and the alkyl iodide promoter by their higher homologues, virtually any carboxylic acid may be produced in a similar way or more carboxylic acids may be produced simultaneously.

In industrial acetic synthesis, methanol feed is continuously fed into the reaction solution together with carbon monoxide. Under the prevailing reaction conditions the catalyst system also catalyses the water gas shift reaction whereby part of the carbon monoxide reacts with the water contained in the reaction solution to form hydrogen and carbon dioxide. Consequently, the reaction system will inevitably contain a finite concentration of hydrogen. Hydrogen will also typically be present in finite amounts in the carbon monoxide feed gas, which is most often produced from synthesis gas consisting of hydrogen and carbon monoxide, e.g. by cryogenic fractionation.

Although the carbonylation process is very selective, typically more than 99% based on methanol, small amounts of by-products being formed, especially propanoic acid, and organic carbonyl impurities like acetaldehyde and acetone, which tend to build up in the synthesis loop.

Primary carbonyl impurities such as acetaldehyde are particularly harmful, because they can react by self condensation to secondary aldol condensation products, such as e.g. croton aldehyde. These secondary aldol condensation products may further react with the iodide catalyst promoters to form organic iodides such as ethyl iodide, butyl iodide and hexyl iodide.

This problem is commonly recognised in the art and mentioned e.g. EP Patent Nos. 487,284, 768,295, 687,662 and U.S. Pat. No. 5,723,660 and references cited therein. In many of these by-products it is difficult to separate from the acetic acid product by conventional means such as distillation because of their boiling points being close to that of acetic acid or due to formation of azeotropes with acetic acid. Additionally, these by-products are known to act as poisons to the catalysts used in downstream processing of acetic acid to e.g. vinyl acetate.

Many attempts have been made to minimise the amount of these by-products in the final acetic acid product, for instance by treatment with ozone (U.S. Pat. No. 5,202,481, EP Patent No. 645,362), by contacting with silver-exchanged ion exchange resins (EP Patent No. 196,173), by contacting with activated carbon (WO 94/22,804), by complicated multiple fractionation of part of raw product stream (WO 98/17,619) in order to avoid excessive build-up of carbonyl impurities in the reaction loop. EP Patent No. 687,662 teaches that the concentration of acetaldehyde in the reaction medium be kept below 400 ppm. This is achieved by removing acetaldehyde, by distillation and subsequent extraction of the acetaldehyde with water, from the process liquid being recirculated to the carbonylation reactor.

In view of the above, a method is desirable that will reduce the formation of carbonyl impurities. One way of achieving this is by in situ catalytic hydrogenation of carbonyl impurities so as to transform e.g. acetaldehyde into ethanol and thereby maintain the acetaldehyde concentration at levels so low that the self-condensation reaction is significantly suppressed.

It is to be noted that, contrary to the carbonyl impurities, by-products propanoic acid (for which ethanol is a precursor) and any higher carboxylic acids may easily be separated from acetic acid by distillation because of the significant difference in boiling points and because propanoic acid does not form azeotropes with acetic acid. Moreover, propanoic acid is a valuable product with a number of industrial applications.

In conventional acetic acid synthesis it is common practice to produce the carbon monoxide feed by cryogenic fractionation of synthesis gas in order to achieve a low content of hydrogen in the feed because hydrogen tends to favour the formation of undesired by-products. Thus, EP Patent No. 728,727 teaches that the content of hydrogen in the carbon monoxide feed being formed in situ by the water gas shift reaction shall preferably be kept less than 2 bar in partial pressure as its presence may result in the formation of hydrogenation products.

The cryogenic separation of carbon monoxide from synthesis gas is a capital and energy intensive process. With less strict demands to the hydrogen content, it is possible to produce carbon monoxide feed more economically, either by carrying out the cryogenic separation to a lower degree of fractionation or by applying e.g. hollow fibre membranes which are commercially available, relatively inexpensive and easy to maintain and operate.

It has now been found that addition of ruthenium compounds to the carbonylation reaction solution conditions effectively reduces the formation of undesired carbonyl impurities whilst increasing the formation of ethanol, ethyl acetate and ethyl iodide being precursors for the formation of valuable propanoic acid.

One of the effects of adding ruthenium compounds to the reaction solution is that the amount of acetaldehyde in the carbonylation reactor is kept at low levels, such as less than 400 ppm.

Accordingly, the present invention provides a process for the carbonylation of methanol and/or reactive derivatives thereof which comprises contacting methanol and/or a reactive derivative thereof with carbon monoxide and hydrogen in the presence of at least (a) a rhodium catalyst, (b) a methyl halide and (c), a ruthenium compound as a hydrogenation catalyst.

When operating the invention the presence of hydrogen is advantageous because it reduces the amount of detrimental carbonyl impurities by converting these into valuable by-products.

The content of hydrogen in the carbon monoxide feed and generated in situ by the water gas shift reaction is preferably above 2 bar in partial pressure and, more preferably, above 3 bar in hydrogen partial pressure to obtain substantial reduction of formation of undesired by-products.

The following examples serve solely as an illustration of the invention:

COMPARISON EXAMPLE 1

A 100 ml Hastelloy B autoclave equipped with a MagneDrive agitator was charged with 10 g acetic acid, 10 g methyl acetate, 7 g methyl iodide, 8 g $H_2O$ and 0.05 g RhI3. The autoclave was vented twice with carbon monoxide, heated to 185° C. and pressurised with carbon monoxide to a total pressure of 3.5 Mpa. The pressure was maintained at 3.5 Mpa by supplying additional carbon monoxide from a reservoir. When the pressure in the carbon monoxide reservoir had decreased from 6.1 MPa to 4.3 MPa, corresponding to about 70% conversion of methyl acetate into acetic acid, the reactor was cooled, depressurized and the liquid was analyzed by gas chromatography. The analysis showed the following distribution of by-products: Acetaldehyde: 344 ppm, acetone 489 ppm, ethyl iodide 25 ppm, ethyl acetate 55 ppm and traces of ethanol.

EXAMPLE 2

The procedure of Comparison Example 1 was repeated except that an additional amount of 0.5 q ruthenium chloride was charged to the reactor. The experiment was conducted exactly as in Comparison Example 1. The resultant liquid mixture contained: 136 ppm acetaldehyde, 451 ppm acetone, 35 ppm ethyl iodide and 83 ppm ethyl acetate.

COMPARISON EXAMPLE 3

Comparison Example 1 was repeated except that the reactor was pressurised with carbon monoxide to 2.5 MPa and, immediately thereafter, further pressurized with hydrogen to a total pressure of 3.5 MPa. The pressure was maintained at 3.5 MPa by supplying carbon monoxide from a reservoir. The reaction was stopped when the carbon monoxide pressure in the reservoir had dropped from 6.8 Mpa to 5.0 Mpa. The following amounts of by-products were found: Acetaldehyde 754 ppm, acetone 459 ppm, ethyl iodide 23 ppm, ethyl acetate 61 ppm and ethanol (trace).

EXAMPLE 4

Comparison Example 3 was repeated except that the reactor was charged with an additional amount of 0.5 g "ruthenium acetate trimer" (Hexakis(acetato)triaquo-i3-oxotriruthenium acetate). The reaction was stopped when the pressure in the carbon monoxide reservoir has dropped from 6.8 MPa to 5.0 MPa. Subsequent analysis showed the reaction liquid to contain 174 ppm acetaldehyde, 128 ppm acetone, 265 ppm ethyl iodide, 713 ppm ethyl acetate and 220 ppm ethanol.

EXAMPLE 5

Example 4 was repeated except that in this experiment the reactor was pressurized with carbon monoxide to 3.0 MPa and thereafter with hydrogen to 3.5 MPa. When the pressure in the carbon monoxide reservoir had decreased from 6.8 MPa to 5.0 MPa the reaction was stopped to yield a solution containing 187 ppm acetaldehyde, 171 ppm acetone, 231 ppm ethyl iodide, 420 ppm ethyl acetate and 82 ppm ethanol.

Examples 1–5 are characterized by relatively high water concentration, about 20 wt %, in the liquid reaction medium. The following Examples 6–9 illustrate the effect of ruthenium at low water concentration.

COMPARISON EXAMPLE 6

Comparison Example 1 was repeated except that only 2 g $H_2O$ was charged to the reactor. The reactor was heated to 185° C. and pressurized to 3.5 MPa with carbon monoxide. When the pressure in the carbon monoxide reservoir had dropped from 6.1 MPa to 4.8 MPa, corresponding to 50% conversion of methyl acetate feed, the reaction was stopped and the liquid analyzed by gas chromatography. The solution contained by-products in the amounts of: 124 ppm acetaldehyde, 295 ppm acetone, 44 ppm ethyl iodide, 84 ppm ethyl acetate.

EXAMPLE 7

Comparison Example 6 was repeated except that the reactor after reaching a temperature of 185° C. was pressurized with carbon monoxide to 2.5 MPa and immediately thereafter pressurized with hydrogen to 3.5 MPa. When the pressure in the carbon monoxide reservoir had dropped from 6.5 MPa to 5.0 MPa, corresponding to 60% methyl acetate conversion the reaction was stopped and the reaction mixture analyzed. The following amounts of by-products were found: Acetaldehyde 493 ppm, acetone 560 ppm, ethyl iodide 55 ppm, ethyl acetate 109 ppm and ethanol (trace).

EXAMPLE 8

Comparison Example 7 was repeated except that an additional amount of 0.5 g "ruthenium acetate trimer" was charged to the reactor. The reactor was heated to 185° C. and pressurized with carbon monoxide to 2.5 MPa and immediately thereafter pressurized with hydrogen to 3.5 MPa. When the pressure in the carbon monoxide reservoir had dropped from 6.4 MPa to 4.9 MPa, corresponding to 60% methyl acetate conversion the reaction was stopped and the reaction mixture analyzed. The following amounts of by-products were found: Acetaldehyde 77 ppm, acetone 63 ppm, ethyl iodide 806 ppm, ethyl acetate 1042 ppm and ethanol (trace).

EXAMPLE 9

Example 8 was repeated in exactly the same manner except that 0.5 g ruthenium chloride, hydrate was used instead of "ruthenium acetate trimer". After this experiment the following amounts of by-products were found: Acetaldehyde 60 ppm, acetone 88 ppm, ethyl iodide 945 ppm, ethyl acetate 889 ppm and ethanol (trace).

EXAMPLE 10

Comparison Example 6 was repeated except that an additional amount of 0.5 g "ruthenium acetate trimer" was charged to the reactor. The reactor was heated to 185° C. and pressurized to 3.5 MPa with carbon monoxide. When the pressure in the carbon monoxide reservoir had dropped from 6.1 MPa to 4.8 MPa, corresponding to 50% conversion of methyl acetate feed, the reaction was stopped and the liquid analyzed by gas chromatography. The following amounts of by-products were found: Acetaldehyde 162 ppm, acetone 431 ppm, ethyl iodide 32 ppm, ethyl acetate 108 ppm and ethanol (trace).

The results of the experiments described in Examples 1–10 are collected in Table 1 (by-products in ppm):

TABLE 1

| Ex | [$H_2O$] wt % | Additive | $P_{H2}$ Mpa | HAc | Acetone | EtI | EtOAc | EtOH |
|---|---|---|---|---|---|---|---|---|
| 1 | 20 | (none) | 0 | 124 | 295 | 44 | 84 | n.d. |
| 2 | 20 | RuCl3, aq | 0 | 136 | 351 | 35 | 83 | n.d. |
| 3 | 20 | (none) | 1.0 | 393 | 560 | 55 | 109 | tr. |
| 4 | 20 | RuOAc | 1.0 | 88 | 31 | 806 | 1042 | tr. |
| 5 | 20 | RuOAc | 0.5 | 101 | 111 | 235 | 420 | 82 |
| 6 | 6 | (none) | 0 | 344 | 489 | 25 | 55 | tr. |
| 7 | 6 | (none) | 1.0 | 754 | 459 | 23 | 61 | tr. |
| 8 | 6 | RuOAc | 1.0 | 174 | 128 | 265 | 713 | tr. |
| 9 | 6 | RuCl3, aq | 1.0 | 160 | 98 | 945 | 889 | tr. |
| 10 | 6 | RuOAc | 0 | 162 | 431 | 32 | 108 | tr. |

MeOAc = methyl acetate,
HAc = acetaldehyde,
EtI = ethyl iodide,
EtOAc = ethyl acetate,
EtOH = ethanol
RuOAc = "ruthenium acetate trimer",
tr. = trace
n.d. = not detected.

The experiments in Examples 1–10 show that addition of ruthenium compounds to the reaction solution in the presence of hydrogen significantly reduces the formation of undesired harmful by-products acetaldehyde and acetone whilst increasing the formation of ethyl iodide, ethyl acetate and ethanol, which are all precursors for propanoic acid.

EXAMPLES 11–13

In addition to the examples above experiments were conducted in a similar manner as in Example 8, but the concentration of the ruthenium acetate hydrogenation catalyst in the reaction medium was varied. The results are listed in Table 2.

TABLE 2

| Ex. | RuOAc g | $P_{H2}$ Mpa | Acetaldehyde ppm | Acetone ppm |
|---|---|---|---|---|
| 11 | 0 | 1.0 | 486 | 556 |
| 12 | 0.15 | 1.0 | 146 | 96 |
| 13 | 0.25 | 1.0 | 112 | 81 |
| 8 | 0.5 | 1.0 | 77 | 63 |

Examples 11–13 show the variation in the amount of harmful by-products, acetaldehyde and acetone, with the amount of added ruthenium hydrogenation catalyst.

EXAMPLES 14–17

Another series of experiments were conducted similarly to that of Example 8 except that the hydrogen partial pressure was varied from 0 to 15 bar. The amounts of acetaldehyde and acetone found in the product solution are displayed ion Table 3.

TABLE 3

| Ex. | RuOAc g | $P_{H2}$ Mpa | Acetaldehyde ppm | Acetone ppm |
|---|---|---|---|---|
| 14 | 0.5 | 0.0 | 162 | 431 |
| 15 | 0.5 | 0.1 | 137 | 370 |
| 16 | 0.5 | 0.3 | 91 | 66 |
| 8 | 0.5 | 1.0 | 88 | 31 |
| 17 | 0.5 | 1.5 | 77 | 28 |

Examples 14–17 show that higher hydrogen partial pressures favours the reduction in the amount of acetaldehyde and acetone in the product solution and that this reduction becomes particularly significant at hydrogen partial pressures of above approximately 2–3 bar.

The above examples demonstrate that the addition of a ruthenium compound as a hydrogenation catalyst to the carbonylation catalyst reaction solution in the presence of hydrogen at a partial pressure of at least 2 bar significantly reduces the formation of harmful carbonyl impurities, acetone and acetaldehyde, which form condensation products, which are difficult to separate from the acetic acid product, whilst at the same time increases the formation of propanoic acid precursors which, under continuous processing under industrial conditions, will eventually become carbonylated into propanoic acid, which is considered a non-harmful, even valuable, product and which may easily be separated from acetic acid by distillation.

EXAMPLE 18

Based on the results obtained in laboratory batch experiments the effect of ruthenium was demonstrated in a continuously operated pilot plant consisting of a carbonylation reactor, a reactor overhead reflux condenser, a flash evaporation separator, a distillation column, a distillation column overhead decanter and a low pressure absorber for the recovery of light ends.

The reactor, containing approximately 550 ppm by weight of rhodium catalyst, was fed with a mixture of methanol, dimethyl ether and water produced in an adjacent pilot plant and carbon monoxide containing between 3–4 vol % hydrogen. From the reactor was withdrawn a liquid product stream consisting mainly of acetic acid, water and methyl iodide, part of which was flash evaporated by reducing the pressure from about 31 barg to about 0.2 barg, causing the temperature to drop from 185° C. to approximately 120° C. The liquid residue containing the rhodium carbonylation catalyst was recycled to the reactor. The gaseous phase from the flash evaporator was introduced to the distillation column together with the dry reactor overhead gas. From the bottom of the distillation column was withdrawn crude acetic acid, from about 99 to about 99.8 wt % in concentration. The distillation column overhead gas was cooled and condensibles separated in the distillation column overhead decanter in which the condensibles separated into an aqueous phase and an organic phase consisting mainly of methyl iodide. The liquid levels in the decanter was maintained by recycling at an approximately constant rate the aqueous and organic phases back to the reactor. The dry gas exiting the decanter was washed countercurrently in the low pressure absorption tower with part of the acetic acid crude product and the liquid phase was returned to the distillation column in order to avoid that methyl iodide and light ends escaped the pilot plant. To ensure stable operation of the pilot plant the volumes of the aqueous and organic phases in the decanter were significantly higher than the liquid volume in the reactor. Thus, the liquid volume contained in the reactor was approximately 5 liters, whereas the liquid volume in each of the two liquid phases in the decanter was at any time between 15 and 20 liters. Both liquid phases contained in the decanter had been used in previous pilot runs and therefore contained a variety of by-products accumulated during past operations.

The pilot plant was operated continuously in this way for approximately 1880 hours. Throughout this period various key process parameters were recorded, some continuously and some at intervals. By chromatographic measurements throughout this period it was shown that the dry gas exiting the reactor overhead reflux condenser at any time contained from 10 to 20% by volume of hydrogen, corresponding to a hydrogen partial pressure in the reactor of between approximately 2–4 bar. During the same period samples of the aqueous phase was withdrawn at intervals from the distillation overhead decanter.

After 1880 hours of operation the methanol feed stream and the aqueous and organic recycle streams from the decanter were gradually reduced and most of the liquid in the synthesis loop were entrained into the distillation column whereby essentially all of the water and methyl iodide and light ends impurities in the synthesis loop were collected in the decanter.

After cooling the reactor the residual liquid in the synthesis loop, containing the rhodium catalyst, were drained off. The reactor was then charged with acetic acid and, additionally, water and methyl iodide from the decanter and thereafter charged with freshly generated catalyst solution containing the rhodium carbonylation catalyst in an amount to produce a rhodium concentration in the reaction solution of between 500 and 600 ppm by weight. Additionally, the reactor was charged with a solution of ruthenium actetate trimer to achieve a final ruthenium concentration in the reaction solution of approximately 4400 ppm by weight. The pilot plant was restarted and reaction conditions similar to the preceeding 1500 hour period were established.

The pilot plant was operated at these conditions for an additional 1220 hours during which period aqueous samples were withdrawn from the decanter at intervals.

Throughout the 3100 hours period the aqueous samples withdrawn from the decanter were analyzed for acetaldehyde by means of gas chromatograpy.

The analyses showed, beyond expectation, a substantial reduction of acetaldehyde concentration in the aqueous phase during the period of time following the change of catalyst system.

During the 3100 hours period of operation a limited number of samples were withdrawn directly from the synthesis loop and subsequently analysed. In the period prior to addition of ruthenium to the synthesis loop the following amounts of acetaldehyde was found in the liquid reaction phase: 460 ppm (333 hrs.); 611 ppm (720 hrs.); 581 ppm (1439 hrs.). After the introduction of the new catalysts system the following values were obtained: 220 ppm (2021 hrs.); 69 ppm (2223 hrs.); 81 ppm (2664 hrs.); 53 ppm (2985 hrs.).

In order to substantiate the data samples of the crude acetic acid product were analysed by GC-MS using a method specifically developed to quantify hexyl iodide down to less than one part per billion (ppb). The same samples were quantified with respect to propanoic acid. The results are displayed in Table 4.

TABLE 4

| Hours on Stream | Hexyl iodide in crude product (ppb) | Propanoic acid in crude product (ppm) |
| --- | --- | --- |
| 220 | 6.8 ± 2 | 1978 |
| 443 | 8.3 ± 2 | 2179 |
| 653 | 8.8 ± 2 | 1669 |
| 911 | 11.2 ± 2 | 1820 |
| 1207 | 13.1 ± 2 | 2117 |
| 1684 | 12.0 ± 2 | 2372 |
| (Change of catalyst). | | |
| 1933 | 8.7 ± 2 | 2345 |
| 2070 | 10.7 ± 2 | 2521 |
| 2109 | 9.4 ± 2 | 2133 |
| 2178 | 5.1 ± 2 | 1888 |
| 2234 | 0.7 ± 0.5 | 2554 |
| 2463 | ≤0.5 | 2290 |
| 2970 | ≤0.5 | 2366 |

The data in table 4 reveal a significant decrease in the amount of hexyl iodide in the crude acetic acid product as well as a less significant increase in the amount of propanoic acid.

I claim:

1. A liquid-phase process for the production of acetic acid, comprising:

contacting methanol or a mixture of methanol and dimethyl ether with carbon monoxide and hydrogen at a partial pressure of hydrogen of at least about 2 bar in a liquid reaction composition consisting essentially of:
(a) a rhodium catalyst;
(b) a methyl halide;
(c) Hexakis(acetato)triaquo-i3-oxotriruthenium acetate; and
(d) water.

2. A liquid-phase process for the carbonylation of methanol and its reactive derivatives, comprising:

contacting methanol, the reactive derivatives thereof, or a mixture of methanol and the reactive derivatives of methanol with carbon monoxide and hydrogen in the presence of a composition consisting essentially of:
(a) a rhodium catalyst;
(b) a methyl halide;
(c) Hexakis(acetato)triaquo-i3-oxotriruthenium acetate; and
(d) water.

3. The process according to claim 2, wherein the partial pressure of hydrogen is at least about 2 bar.

* * * * *